United States Patent [19]
Allen

[11] Patent Number: 5,341,816
[45] Date of Patent: Aug. 30, 1994

[54] BIOPSY DEVICE

[76] Inventor: William C. Allen, 4801 Vineyard Way, Rte. 3, Columbia, Mo. 65203

[21] Appl. No.: 989,476

[22] Filed: Dec. 7, 1992

Related U.S. Application Data

[63] Continuation of Ser. No. 869,209, Apr. 13, 1992, abandoned, which is a continuation of Ser. No. 432,132, Nov. 6, 1989, abandoned.

[51] Int. Cl.$^5$ .............................................. A61B 10/00
[52] U.S. Cl. ................................. 128/754; 606/170; 606/179; 606/180
[58] Field of Search ................ 128/749, 751, 754; 606/167, 170, 179, 180; 30/113.1, 113.2, 113.3, 124, 278, 316

[56] References Cited

U.S. PATENT DOCUMENTS

| | | | |
|---|---|---|---|
| 1,371,948 | 3/1921 | Szütz | 30/316 |
| 2,919,692 | 1/1960 | Ackerman . | |
| 3,577,979 | 2/1968 | van der Gaast | 128/754 |
| 3,850,158 | 11/1974 | Elias et al. . | |
| 3,893,445 | 7/1975 | Hofsess . | |
| 3,913,566 | 10/1975 | Lacey | 128/754 |
| 4,099,518 | 7/1978 | Baylis | 30/113.1 |
| 4,262,676 | 4/1981 | Jamshidi | 128/754 |
| 4,306,570 | 12/1981 | Matthews . | |
| 4,314,565 | 2/1982 | Lee | 128/754 |
| 4,696,308 | 9/1987 | Meller et al. | 128/754 |
| 4,798,213 | 1/1989 | Doppelt | 30/278 |
| 4,838,282 | 6/1989 | Strasser et al. . | |
| 4,873,991 | 10/1989 | Skinner | 128/754 |

OTHER PUBLICATIONS

Johnson, et al.–Pectaneous Biopsy of the Iliac Crest (Mar.–Apr. 1977).
Sacker, et al.–A Simple Bone Biopsy Needle (date unknown).
Duursma, et al.–A Bone Biopsy Procedure (1969).

*Primary Examiner*—Randy Shay
*Attorney, Agent, or Firm*—Fish & Richardson

[57] ABSTRACT

A biopsy device for obtaining biopsy specimens from hard or soft tissue includes a biopsy extracting member which may be inserted into a cannula and a removable biopsy specimen holder which is preferably threaded into the biopsy extracting member. The specimen holder preferably includes a cutting edge (e.g., serrated for hard tissue, slicing for soft tissue), and retaining fishscales or scallop members for securely holding The biopsy specimen. Once the biopsied specimen is cut from the tissue, it may be sent, within the removable specimen holder, to the pathologist for analysis.

20 Claims, 1 Drawing Sheet

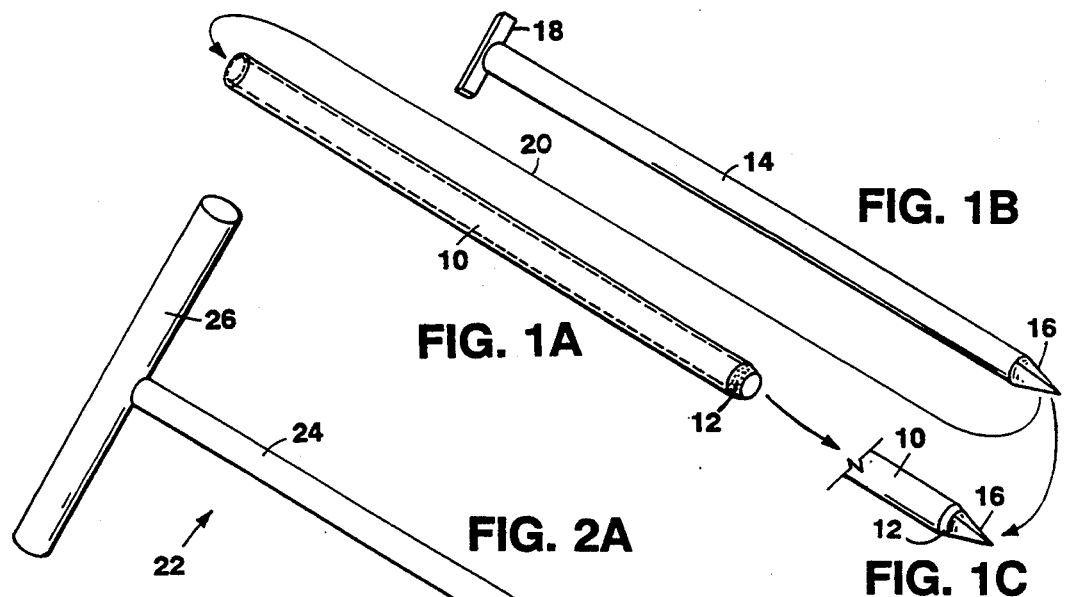
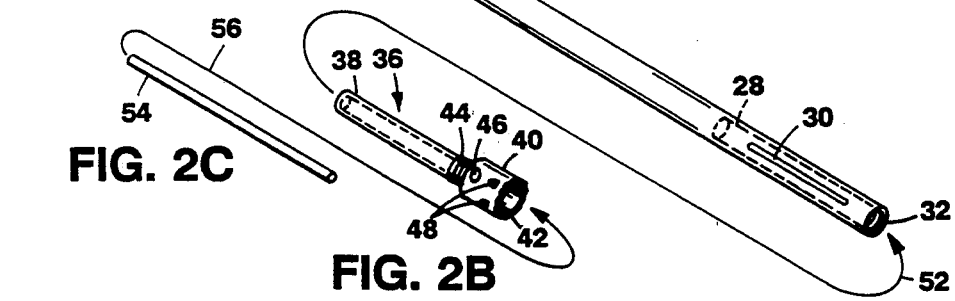
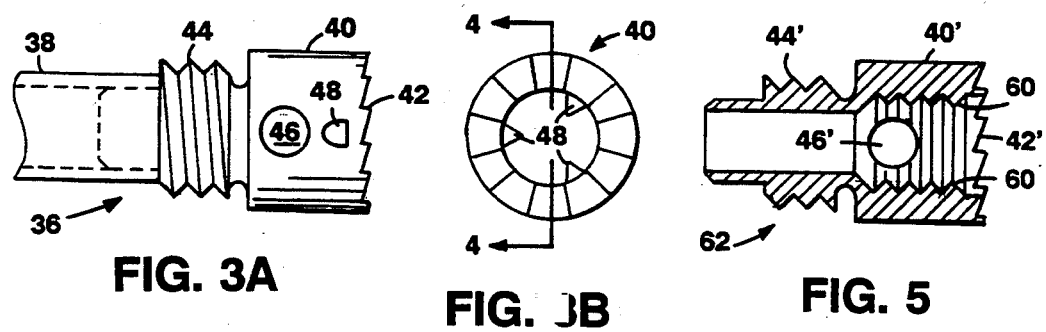
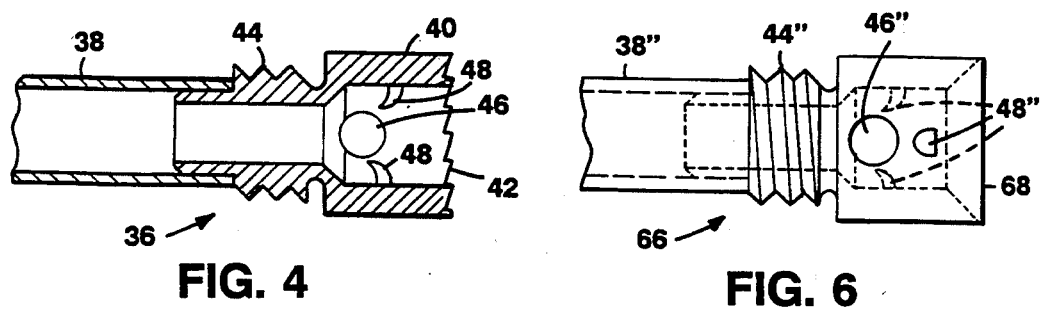

BIOPSY DEVICE

This is a continuation of application Ser. No. 07/869,209, filed Apr. 13, 1992, now abandoned which is a continuation of Ser. No. 07/432,132 filed Nov. 6, 1989, now abandoned.

BACKGROUND OF THE INVENTION

The present invention relates to devices for taking hard tissue or soft tissue biopsy specimens.

Biopsies are taken when a small tissue specimen is required for examination, e.g., by a pathologist, particularly in cases where cancer is suspected.

More than one million tissue (hard and soft) biopsies are presently performed each year in the United States. Soft tissue biopsies are performed by surgeons of all specialties as well as by some oncologists. Hard tissue (bone) biopsies are performed primarily by three types of physicians: orthopaedic surgeons, oncologists (usually orthopaedic), and radiologists. Although the vast majority of all biopsies performed are of soft tissue biopsies, the number of bone biopsies has been growing rapidly over the past few years. Biopsies are used in both human and veterinary medicine.

Summary of the Invention

A general feature of the invention is a biopsy device for obtaining either hard (bone) or soft tissue biopsy specimens including a biopsy extracting member adapted for insertion into a cannula, and a biopsy specimen holder removably attached, preferably by threaded engagement, to one end of the biopsy extracting member. In a preferred embodiment, the specimen holder has an inside diameter on the order of 2.4 mm. (1.2 mm. in a sternal version), and includes an elongated, substantially transparent, plastic tubular portion which fits within the biopsy extracting member and a cutting portion, having either a serrated or slicing edge, which extends from one end of the biopsy extracting member. In another preferred embodiment, the biopsy extracting member includes a handle and at least one viewing portal for viewing a biopsy specimen held within the tubular portion of the specimen holder. Preferably also, the specimen holder includes a plurality of inwardly extending scallop-like retaining members formed by perforations in the cutting portion, or fishscale-like retaining members formed by machining material from the interior of the cutting portion, either of which is adapted to inhibit movement of the biopsy specimen in at least one longitudinal direction. The biopsy device also preferably includes a sharply pointed starter trocar (obturator) which may be inserted into the cannula in place of the biopsy extracting member.

Another general feature of the invention is a method for obtaining either a soft or hard tissue biopsy specimen from a surgical site, which includes the steps of inserting a sharply-pointed starter trocar into a cannula, whereby the sharply pointed end of the trocar extends from the cannula; pushing the cannula-enclosed starter trocar into the surgical site; removing the starter trocar from the cannula; inserting a biopsy extracting member having a removable specimen holder into the cannula, the specimen holder having a cutting portion which extends from the biopsy extracting member twisting the biopsy extracting member within the cannula against tissue, whereby the tissue is cut by the cutting portion and the cut tissue is held within the specimen holder; removing the biopsy extracting member from the surgical site; removing the specimen holder from the biopsy extracting member and pushing the tissue out of the specimen holder, whereby the tissue may be examined by a pathologist. Preferred methods of performing the invention include pushing the cannula-enclosed starter trocar against a bone, sawing the bone with the cutting portion, and unscrewing the specimen holder from said biopsy extracting member in advance of pathological examination.

DESCRIPTION OF THE PREFERRED EMBODIMENTS

The drawings are first briefly described:

FIGS. 1A-1C are perspective views showing the interrelationship among two components of a biopsy device in accordance with a preferred embodiment of the present invention;

FIGS. 2A-2C are perspective views showing the interrelationship among three further components of a biopsy device in accordance with a preferred embodiment of the present invention;

FIGS. 3A-3B are side elevation and end views, respectively, of a portion of a biopsy device in accordance with a preferred embodiment of the present invention;

FIG. 4 is a cross-sectional view of a portion of a biopsy device taken along-the line 4—4 of FIG. 3B;

FIG. 5 is a cross-sectional view of a portion of a biopsy device in accordance with an alternate preferred embodiment of the present invention;

FIG. 6 is a schematic view, with internal structure in phantom, of a portion of a biopsy device in accordance with another preferred embodiment of the present invention.

STRUCTURE

FIGS. 1A-4 depict one embodiment of a biopsy device in accordance with the present invention. Referring to FIGS. 1A-1C, there is a hollow, cylindrical cannula 10 having a tapered end 12. A solid cylindrical starter trocar 14, having a sharply pointed end 16 and a stop member 18, is insertable into the cannula 10 as indicated by assembly arrow 20. The stop member 18 serves to limit the extent to which the sharply pointed end 16 of the starter trocar 14 extends from the cannula 10, as can be most clearly seen from FIG. 1C.

Referring to FIG. 2A, there is a biopsy extracting member 22 having cylindrical body portion 24 and a T-handle end 26. The biopsy extracting member 24 is insertable into the cannula 10. The end of the body portion 24 opposite the T-handle end 26 is hollow, as shown by the dashed line 28 in FIG. 2A. There are a pair of longitudinal slots 30 or viewing portals in the sidewall of the biopsy extracting member 22 in the vicinity of the hollow area 28, and there is an internal thread 32 at the end of the biopsy extracting member.

The cannula 10, starter trocar 14, and biopsy extracting member 22 are all fabricated from surgical-grade stainless steel, and can all be used to obtain either hard tissue or soft tissue biopsy specimens.

Referring to FIGS. 2B, 3A, 3B, and 4, there is a disposable bone blade/cartridge assembly 36. The cartridge assembly 36 includes an elongated clear plastic tubular portion 38 and a stainless steel cutting portion 40. The cutting portion 40 has a serrated cutting edge 42, an external thread 44, a pair of holes 46, and a plurality of scallop retaining members 48.

As can be most clearly seen from FIGS. 3A, 3B and 4, the scallop retaining members 48 which are formed by perforations in the wall of the cutting portion 40, extend inwardly and away from the serrated cutting edge 42. Thus, they permit a biopsy specimen to easily slide into the cartridge assembly 36, but act to prevent the specimen from sliding out of the cartridge, e.g., when the biopsy extracting member is removed from the bone.

As indicated by assembly arrow 52, the blade/cartridge assembly 36 may be removably attached to the biopsy extracting member 24 by inserting the tubular portion 38 into the hollow area 28 and engaging external thread 44 with internal thread 39. The holes 46 facilitate disassembly of the blade/cartridge assembly 36 from the biopsy extracting member 24, by permitting a pin (not shown) to be inserted therein to serve as a lever to aid in unscrewing the cartridge assembly from the extracting member.

Referring to FIG. 2C, a plastic pusher 54 is shown which, in accordance with assembly arrow 56, may be inserted into the cartridge assembly 36 to push out the biopsy specimen.

As an alternative to the scallop retaining members 48 fishscale retaining members 60 may be used as shown in the alternate embodiment of a bone blade/cartridge assembly 62 of in FIG. 5. Except for the use of fishscale retaining members 60 in place of scallop retaining members 48, the bone blade/cartridge assembly 62 corresponds generally to the bone blade cartridge assembly 36, and includes a cutting portion 40', a serrated cutting edge 42', an external thread 44', and a pair of holes 46', all of which correspond respectfully to the elements 40, 42, 44 and 46 of the bone blade/cartridge assembly 36. The fishscale retaining members 60 are formed by machining annular grooves into the interior surface of the cutting portion 40' of the bone blade/cartridge assembly 62. As shown, the fishscale retaining members 60 extend inwardly and away from the serrated cutting edge 42'.

Referring now to FIG. 6, there is a soft-tissue blade/cartridge assembly 66 in accordance with an alternate embodiment of the present invention. The soft-tissue blade/cartridge assembly 66 is generally similar to the bone blade/cartridge assembly 36, and may be threaded into the biopsy extracting member 22. The major difference between the bone blade/cartridge assembly 36 and the soft-tissue blade/cartridge assembly 66 is that the former has a serrated cutting edge 42 for sawing through bone, whereas the latter has a sharp knife-like slicing edge 68 for cutting soft tissue. Otherwise, the soft-tissue blade/cartridge assembly 66 includes a clear plastic tubular portion 38", an external thread 44", a pair of holes 46" to assist in unscrewing, and a plurality of scallop retaining members 48", all of which correspond generally to the elements 38, 44, 46 and 48 of the bone blade/cartridge assembly 36.

PROCEDURE

For either bone or hard tissue, the patient is first properly positioned, a surgical scrub done and, using the proper anesthetic in the proper setting (such as the operating room or clinic), a small incision is made in the skin. Aseptic technique is used throughout the procedures.

Use of the biopsy device of the present invention to obtain a bone biopsy specimen is first described.

The starter trocar 14 is first inserted into the cannula 10 with the sharp end 16 of the starter trocar extending from the cannula. The sharp end 16 is then inserted into the incision at the surgical site and gently pushed through the soft tissues until it abuts bone. The cannula 10 is then slipped down over the starter trocar 14 the last few millimeters until it is also abutting bone. A bone blade/cartridge assembly 36 has previously been screwed onto the end of the biopsy extracting member 22 opposite the T-handle end 26. The starter trocar 14 is then removed from the cannula 10, and the biopsy extracting member 22 inserted down to the bone.

The operator then holds the cannula 10 snugly against the bone and begins twisting the biopsy extracting member 22 in a clockwise motion, holding onto the T-handle end 26. Gentle pressure is applied so that the serrated cutting edge 42 cuts through the cortical aspect of the bone, pushing a core biopsy of bone and underlying cancellous bone into the bone blade/cartridge assembly 36 as the biopsy extracting member 22 advances into the bone.

When the proper depth has been reached, the operator continues to hold the cannula 10 snugly against the bone and removes the biopsy extracting member 22 by pulling on the T-handle end 26 and removing it from the bone. Gentle clockwise motion may facilitate removal of the biopsy extracting member. Counterclockwise motion should be avoided as it potentially could cause the blade/cartridge assembly 36 to unscrew from the biopsy extracting member 22.

The longitudinal slots 30 in the end of the biopsy extracting member 22 permit viewing of the clear plastic tubular portion 38 of the bone blade/cartridge assembly 36 allowing the operator to observe that a tissue specimen has been obtained. The scallop retaining members 48 along the inner surface of the bone blade/cartridge assembly 36 (or alternatively, the fishscale retaining members 60 in the event the alternate bone blade/cartridge assembly 62 is used) allows the biopsied bone specimen to slide into the cartridge easily; but, because of the shape of the scallop (or fishscale) retaining members, the bone is securely held in the cartridge when the biopsy extracting member 22 is pulled out of the bone. The bone blade/cartridge assembly 36, containing the biopsied bone specimen, is then unscrewed from the biopsy extracting member 22 and sent to the pathologist with the biopsy tissue intact within the cartridge.

The pathologist then inserts the plastic pusher 54 into the serrated cutting edge end (42) of the bone blade/cartridge assembly 36 to remove the biopsy specimen. By obtaining the bone biopsy in this method, the pathologist can better understand the normal alignment of the bony tissue which is biopsied. The bone blade/cartridge assembly 36 may then be discarded. By so doing, a new sharp blade is available for use for each biopsy.

Essentially, the same procedure is used for obtaining soft tissue biopsy specimens. The only difference being that the soft-tissue blade/cartridge assembly 66 is used in place of the bone blade/cartridge assembly 36. The soft-tissue blade/cartridge assembly 66 has a sharp cutting or slicing edge 68 instead of a serrated cutting edge 42, making the biopsy of soft tissue easier,

What is claimed is:

1. A biopsy device comprising:
   a biopsy extracting member having a hollow interior portion and a substantially smooth generally cylindrical exterior whereby it may closely slidingly fit within a generally cylindrical cannula; and a biopsy specimen holder removably attached to one end of said biopsy extracting member, said specimen holder including an elongated tubular specimen receiving portion which is open at both ends, a portion which fits within and engages said extracting member, and a cutting portion which extends from said one end of said biopsy extracting member;

whereby when said specimen holder is detached from said biopsy extracting member a pusher member having an elongated generally cylindrical shape and being sized to closely slidingly fit within said specimen receiving portion of said specimen holder may be used to remove any biopsy specimen contained within said specimen holder without opening said specimen holder.

2. The biopsy device of claim 1 wherein both said biopsy extracting member and said specimen holder are threaded, whereby said removable attachment may be achieved by engagement of the threads on said biopsy extracting member with the threads on said specimen holder.

3. The biopsy device of claim 1 wherein said cutting portion includes a serrated cutting edge.

4. The biopsy device of claim 1 wherein said cutting portion includes a slicing edge.

5. The biopsy device of claim 1 wherein said elongated tubular portion is substantially transparent.

6. The biopsy device of claim 5 wherein said biopsy extracting member includes at least one viewing portal adjacent said tubular portion when said specimen holder is attached to said biopsy extracting member, whereby a specimen held within said specimen holder may be viewed.

7. The biopsy device of claim 5 wherein said elongated tubular portion is plastic.

8. The biopsy device of claim 1 wherein said biopsy extracting member, further includes a handle at the end opposite said one end.

9. The biopsy device of claim 1 wherein said specimen holder includes at least one inwardly extending retaining member adapted to inhibit movement of any specimen contained within said specimen holder in at least one longitudinal direction.

10. The biopsy device of claim 9 wherein said specimen holder includes a plurality of inwardly extending scallop retaining members formed by perforations in said cutting portion.

11. The biopsy device of claim 9 wherein said specimen holder includes a plurality of inwardly extending fishscale retaining members formed by machining the interior surface of said cutting portion.

12. In a kit for obtaining biopsy specimens of the type including a generally cylindrical cannula, and a sharply pointed starter trocar adapted to closely slidingly fit within the cannula, the improvement comprising:

a biopsy extracting member having a hollow interior portion and a substantially smooth generally cylindrical exterior to closely slidingly fit within the cannula; and a biopsy specimen holder removably attached to one end of said biopsy extracting member, said specimen holder including an elongated one-piece tubular specimen receiving portion which is open at both ends, a portion which fits within and engages said extracting member, and a cutting portion which extends from said one end of said biopsy extracting member.

13. The biopsy kit of claim 12 wherein said cutting portion has a serrated cutting edge which extends from said one end of said biopsy extracting member.

14. The biopsy kit of claim 12 wherein said specimen holder includes an elongated tubular portion adapted to fit within said biopsy extracting member, and a cutting portion having a slicing edge which extends from one end of said biopsy extracting member.

15. The biopsy kit of claim 12 wherein said specimen holder includes a plurality of perforations forming inwardly extending retaining members.

16. An apparatus for obtaining hard tissue biopsy specimens comprising:

a holding member having a substantially smooth exterior surface of circular cross section whereby it may closely slidingly fit within a generally cylindrical cannula and a generally cylindrically shaped hollow interior portion extending into said holding member from one end thereof, and a biopsy specimen holder having a generally cylindrically shaped hollow specimen receiving portion which is open at both ends and a portion which fits within and engages said hollow interior portion of said holding member so that said specimen holder is removably attachable to said holding member, whereby when said specimen holder is detached from said holding member a pusher member having an elongated generally cylindrical shape and being sized to closely slidingly fit within said specimen receiving portion of said specimen holder may be used to remove any biopsy specimen contained within said specimen holder without opening said specimen holder.

17. The biopsy kit of claim 16 wherein said specimen holder is removably attachable to said holding member by threaded engagement.

18. The biopsy kit of claim 16 wherein said specimen holder includes a serrated cutting edge.

19. The biopsy kit of claim 16 wherein said specimen holder includes at least one inwardly extending retaining member adapted to inhibit movement of any specimen contained within said specimen holder in at least one longitudinal direction.

20. The apparatus of claim 16 wherein said holding member is a T-shaped handle.

* * * * *